United States Patent [19]

Kemp et al.

[11] Patent Number: 5,116,755
[45] Date of Patent: May 26, 1992

[54] **ASEXUAL BLOOD STAGE ANTIGENS OF *PLASMODIUM FALCIPARUM* WHICH ENCODE A RHOPTRY PROTEIN**

[76] Inventors: David J. Kemp, 309 Belmore Road, North Balwyn, 3104, Victoria; Robin F. Anders, 55 Brougham Street, North Melbourne, 3051, Victoria; Ross L. Coppel, 6 Mercer Road, Armadale, 3143, Victoria; Graham V. Brown, 35 Walsh Street, Balwyn, 3103, Victoria, all of Australia

[21] Appl. No.: 131,137
[22] PCT Filed: Dec. 18, 1986
[86] PCT No.: PCT/AU86/00386
  § 371 Date: Aug. 25, 1987
  § 102(e) Date: Aug. 25, 1987
[87] PCT Pub. No.: WO87/03882
  PCT Pub. Date: Jul. 2, 1987

[30] Foreign Application Priority Data

Dec. 24, 1985 [AU] Australia .................. PH4021

[51] Int. Cl.[5] .............. C12P 21/06; C12P 19/34; C12N 15/00; C12N 5/00; C12N 15/30; C12N 15/70; C12N 1/21; C07H 15/12; C07K 3/00
[52] U.S. Cl. .............. 435/252.3; 435/69.8; 435/91; 435/172.3; 435/240.1; 435/252.33; 435/320.1; 536/27; 530/350; 935/18; 935/27; 935/31; 935/41; 935/48; 935/56; 935/58; 935/65; 935/18; 935/73; 935/81
[58] Field of Search ............ 435/68, 709.1, 192.1, 435/172.3, 252.33, 235, 320, 69.8, 71.2, 69.8, 252.3, 240.1, 240.2, 320.1; 536/77; 530/350; 935/18, 31, 41, 58, 65, 73, 81

[56] References Cited

PUBLICATIONS

Odink et al. FEBS Lett vol. 173 pp. 108–112 (1984).
Kemp et al. Proc. Nat'l Acad Sci USA vol. 80 pp. 3787–3791 (1983).

*Primary Examiner*—Richard A. Schwartz
*Assistant Examiner*—Jean Ellis

[57] ABSTRACT

DNA molecules comprising artificially constructed polynucleotide sequences substantially coresponding to all or a portion of the base sequence coding for an antigen of *Plasmodium falciparum* selected from the group consisting of the Acidic Basic Repeat Antigen Rhoptry (ABRA), the antigen of any of clones Ag 169, Ag303, Ag358, Ag361, Ag372, Ag394 or Ag501, defined herein, and other antigens of *P. falciparum* cross-reactive therewith. Such DNA molecules are capable of being expressed as polypeptide(s). Synthetic peptides or polypeptides displaying the antigenicity of all or a portion of the above antigens of *P. falciparum*. Compositions for stimulating immune responses against *P. falciparum* antigens in a mammal, comprising at least one polyupeptide displaying the antigenicity of the above antigens of *P. falciparum*, together with a pharmaceutically acceptable carrier therefor.

8 Claims, 17 Drawing Sheets

```
     ValAspIleLeuGluGluLysThrLysAspGlnAspLeuGluIleGluLeuTyrLysTyr
     GCGTTGACATATTAGAAGAAAAAACCAAGGATCAAGATTTAGAAATAGAATTATACAAATAT
         10        20        30        40        50        60

MetGlyProLeuLysGluGlnSerLysSerThrSerAlaAlaSerThrSerAspGluLeuSer
     ATGGGACCATTAAAAGAACAATCTAAAAGTACAAGTGCTGCATCTACTAGTGATGAATTATC
         72        82        92       102       102       122

GlySerGluGlyProSerThrGluSerThrSerThrGlyAsnGlnGlyGluAspLysThrThr
     AGGTTCTGAAGGTCCATCTACTGAATCTACAAGTACAGGAAATCAAGGTGAAGATAAAACAA
        134       144       154       164       174       184

AspAsnThrTyrLysGluMetGluGluLeuGluGluAlaGluGlyThrSerAsnLeuLys
     CAGATAATACATACAAAGAAATGGAAGAATTAGAAGAAGCTGAAGGAACTTCAAATCTTAAA
        196       206       216       226       236       246

LysGlyLeuGluPheTyrLysSerSerLeuLysLeuAspGlnLeuAspLysGluLysProLys
     AAAGGTTTAGAATTTTATAAATCTTCTCTAAAACTTGATCAATTAGATAAAGAAAAACCTAA
        258       268       278       288       298       308

LysLysLysSerLysArgLysLysLysArgAspSerSerSerAspArgIleLeuLeuGluGlu
     AAAGAAAAAATCTAAAAGAAAAAAAAGAGAGACAGTTCTAGTGACAGAATATTATTAGAAG
        320       330       340       350       360       370

SerLysThrPheThrSerGluAsnGluLeuxxx
     AATCTAAAACCTTTACTTCTCAAAATGAATTGTAAATTAAAAATTTAATCCTACATGTAGAT
        382       392       402       412       422       432

TTTATTATATTACATCATGTAATCATATTATAGAATTTATTTTTAAGAAAAAAAAAAAAA
        444       454       464       474       484       494
```

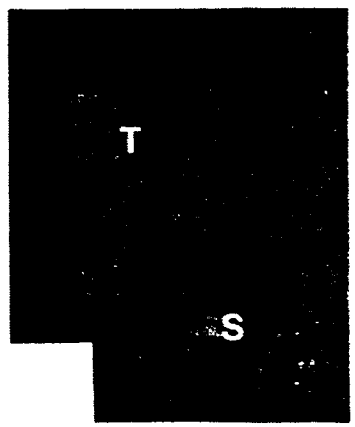
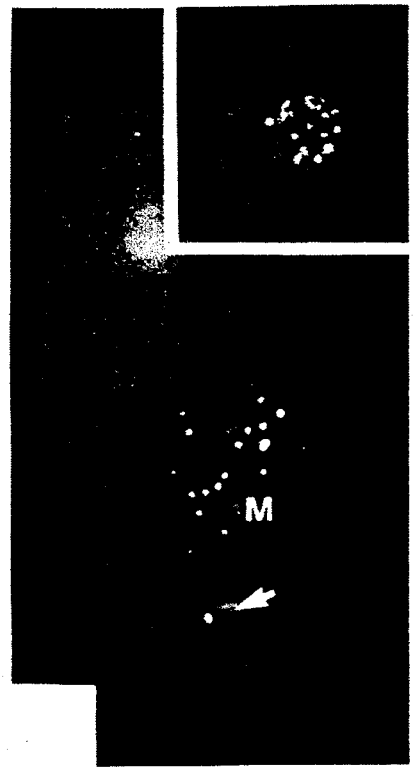
FIG. IA
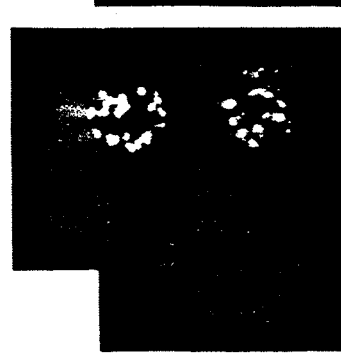
FIG. IB
FIG. IC
FIG. 2

FIG. 4.

```
           ValAspIleLeuGluGluLysThrLysAspGlnAspLeuGluIleGluLeuTyrLysTyr
           GCGTTGACATATTAGAAGAAAAACCAAGGATCAAGATTAGAAATAGAATTATACAAATAT
                    10        20        30        40        50        60

MetGlyProLeuLysGluGlnSerLysSerThrSerAlaAlaSerThrSerAspGluLeuSer
ATGGGACCATTAAAAGAACAATCTAAAAGTACAAGTGCTGCATCTACTAGTGATGAATTATC
         72        82        92       102       112       122

GlySerGluGlyProSerThrGluSerThrGluSerThrGlyAsnGlnGlyGluAspLysThrThr
AGGTTCTGAAGGTCCATCTACTGAATCTACAAGTACAGGAAATCAAGGTGAAGATAAAACAA
         134       144       154       164       174       184

AspAsnThrTyrLysGluMetGluGluIleLeuGluGluAlaGluGlyThrSerAsnLeuLys
CAGATAATACATACAAAGAAATGGAAGAAATTAGAAGAAGCTGAAGGAACTTCAAATCTTAAA
         196       206       216       226       236       246

LysGlyLeuPheTyrLysGluPheTyrLysSerLeuAspLysAspLysSerGlnLeuAspGlnLeuLysSerProLys
AAGGTTTAGAATTTTATAAATCTCTTAAAACTTGATAATTAGATAAAGAAAACTTAA
         258       268       278       288       298       308

LysLysSerLysLysLysArgLysLysLysLysArgAspSerSerAspArgIleLeuLeuLeuGluGlu
AAAGAAAAATCTAAAAGAAAAAAAAGAGAGACAGTTCTAGTGACAGAATATTATTAGAAG
         320       330       340       350       360       370

SerLysThrPheThrSerGluAsnGluLeuxxx
AATCTAAAACCTTTACTTCTCAAAATGATGATAAAAATTAAAAATTAATCCTACATGTAGAT
         382       392       402       412       422       432

TTTATTTATATTACATCATGTAATCATATTATAGAATTATTTTTAAGAAAAAAAAAAAAA
         444       454       464       474       484       494
```

```
HisTyrLysLysArgLysAlaGlnGluLysGlyLeuProGluPro
CATTATAAGAAAAAGAAAAAGCTCAAGAAAAAGGATTACCAGAACCTACTGTTACTAATGAA
         10        20        30        40        50        60

GluTyrValGluGluLeuLysLysGlyIleLeuAspMetGlyIleIleLysLeuPheSer
GAATATGTTGAAGAATTAAAGAAAGGTATTCTAGATATGGGTATCAAATTATTATTTAGT
         70        80        90       100       110       120

LysValLysSerLeuLeuLysLysAsnLysIleProLysLysGluAsp
AAAGTTAAAAGCCTATTAAAAAAGAATAAAATATTCCTAAGAAAAAAGAAGAT
        130       140       150       160       170       180

AsnGlnAlaValAspThrLysSerMetGluGluProLysValLysAlaGlnProAlaLeu
AATCAAGCAGTAGATACCAAAAGTATGGAAGAACCAAAGGTTAAAGCACAACCAGCTCTT
        190       200       210       220       230       240

ArgGlyValGluProThrGluAspSerAsnIleMetAsnSerIleAsnAsnValMetAsp
AGAGGTGTTGAACCAACGGAAGATTCTAATATTATGAACAGTATTAATAATGTTATGGAT
        250       260       270       280       290       300

GluIleAspPhePheGluLysGlyLeuIleGluAsnAsnThrProAsnValValPro
GAAATTGATTTCTTTGAAAAAGAATTAATCGAAAATAATACACCTAATGTTGTTACCA
        310       320       330       340       350       360
```

FIG. 8A.

```
ProThrGlnSerLysLysLysAsnLysAsnGluThrValSerGlyMetAspGluAsnPhe
CCAACTCAATCAAAAAAAAAAAACAAAAATGAAACTGTATCTGGTATGGATGAAATTT
         370            380           390           400     ↑    410           420
                                                          Ag 144

AspAsnHisProGluAsnTyrPheLysGluGluTyrTyrAspGluAsnAspAspMet
GATAATCATCCTGAAAATTATTTTAAAGAAGAATATTATTATGATGAAAATGATGATATG
         430           440            450            460  Ag 126/ 470          480
                                                                 Ag 196

GluValLysValLysLysIleGlyValThrLeuLysLysPheGluProLeuLysAsnGly
GAAGTAAAAGTTAAAAAAATAGGTGTCACATTAAAAAAATTTGAACCACTTAAAAATGGA
         490            500            510            520            530            540

AsnValSerGluTyrIleLysLeuIleHisLeuGlyAsnLysAspLysLysHisIleGlu
AATGTTAGTGAAACCATTAAATTGATTCATTTAGGAAATAAAGATAAAAAACACATTGAA
         550            560            570            580            590            600

AlaIleAsnAsnAspIleGlnIleIleLysGlnIleGluLeuGlnAlaIleTyrAsnGluLeu
GCTATAAACAACGATATTCAAATTATTAAACAAGAATTACAAGCTATTTATAATGAACTT
         610            620            630            640            650            660

MetAsnTyrThrAsnGlyAsnLysAsnIleGlnGlnGlnIlePheGlnGlnAsnIleLeuGlu
ATGAATTATACAAATGGAAACAAAAATATTCAACAAAATATTTCAACAAAATATTCTAGAA
         670            680            690            700            710            720
```

FIG. 8B.

```
AsnAspValLeuAsnGlnGluThrGluGluMetGluLysGlnValGluAlaIleThr
AATGATGTTCTTAATCAAGAAACGGAGGAAGAAATGGAAAACAAGTTGAAGCAATCACC
         730           740           750           760           770           780

LysGlnIleGluAlaGluValAspAlaLeuAlaProLysAsnLysGluGluGluLys
AAGCAAATAGAAGCTGAAGTGGATGCCCTCGCACCAAAAAATAAGGAAGAAGAAAAA
         790           800           810           820           830           840

GluLysGluLysGluLysGluLysGluLysGluLysGluLysGluLysGluLysLys
GAAAAAGAAAAAGAAAAAGAAAAAGAAAAAGAAGAAAAGAAAAAGAAAAAGAAAAA
         850           860           870           880           890           900

GluGluLysGluLysGluLysGluLysGluLysGluLysGluLysGluLysGluLys
GAAGAAAAGAAAAAGAAAAAGAAGAAAAAGAAAAGAAGAAGAAGAAGAAGAAAAA
         910           920           930           940           950           960

LysAsn
AAAAA
```

FIG.8C.

```
  10         20         30         40         50         60         70
TCCTCTCTTCCTCTCTTCCTCTCTTCCTCTCTTCCTCTCTTCATCTTCTTCATCTTCTTCTTCTACTTCTCT
                                80         90        100
                        TCATCTTCTTGTACCTCTTTAGATTCTTCT
 210        220        230        240        250        260        270
TATCTCTTTGGGTACTACAGTTCCTATGGTACCTATTAATTGCTCTTGTATGGATAAGTTTT
                               280        290        300
                        TTCTTCAACTTTTGATTATCCATTAATGT
 410        420        430        440        450        460        470
TTTATTATTTCTACACCATCTTTGTCTTCATCTTCTATAACATTTTTAACTACGTGTTTTTTTACTTTTT
                               480        490        500
                        CTTTTTTTGCTTTTTTATGTTTTCCTTTAT
 610        620        630        640        650        660        670
TCCTCTTCTTTGTGTTCTCTCCTTCTTGTGTTCTTCTTCTTGTGTTCTCCTTCTCTTGGTGTTCTTGGTGTA
                               680        690        700
                        GTTACGTCTGTCAATGGACTTGGTAATGGT
 810        820        830        840        850        860        870
AAAAAAAAAAAAAAAAAAAAAAAAAAAAAA
                              880        890        900
```

FIG. 10A.

```
       110        120        130        140        150        160       170
TGTACCTTCTTTAGATTCTTCTTTTTGTCTTCTTCCTTATCAACATGTTTCTGTTTTGAAGTTCAGCTT
       310        320        330        340        350        360       370
TAATTGTTCTGGTTCATCTATTAGTTTACATTGTGGGTTGGCTTAGTGGTCTACTTTCTACTGTTATGT
       510        520        530        540        550        560       570
CTTTCTTTCCTTATCTTTGATTTGTTCTTTGATTTGTGTCTTCTTTTTGTTC
       710        720        730        740        750        760       770
ACCATAAATTTCATTGTTGGTTTCTTCACTTGTTGATCGGTGTTGCATTGTTCTTCATTTTCCTTAT
        910        920        930        940        950        960       970

180        190        200
                            CCTCTATCTTCGCCATTTTTTCTTATGAT
                                    380        390        400
                            TGTTCTTCACATGCCTCTTATCTTCTAAG
                                    580        590        600
                            TTCTTCTTGTGTTCTTCTTCTTTGTGTTC
                                    780        790        800
                            CATGTTTTATTAATATATGATTAATTAAAA
                                    980        990       1000
```

FIG. 10B.

```
                10                 20                 30                 40                 50                 60                 70
     GAATTCGAG AGTCAAAGT TCTAGTCAC AGTTCTAGTT CAAGTTCAGA AGTCTTCCT GCTAATGGAC CT
        82          92         102        112        122        132        142
     GATTCCCCTA CTGTTAAACC GCCAAGAAAT TTACAAAATA TATGTGAAAC TGGAAAAAAC TTCAAGTTCC TA
        154        164        174        184        194        204        214
     GTATATATTA AGGAGAATAC ATTAATACTT AAATGGAAAG TATACGGAGA AACAAAGAA TACTACTGAA AA
        226        236        246        256        266        276        286
     TAACAAAGTT G
```

*FIG. 11.*

AATAAT-CAAAACAATAATGGAAAGTGTAAACATATAATAATCAAAGGATTTAATAA

ATAACTATTTTAATAATAATAATAATAATAATAACAATATGCCAAATATATTCTAGT

GAATATGTACA-GAACATATTATAACACACATATGAATCATTCATAATGATAATAAGGAA

TTATCATATTGATGATTCAAAAGAATGTTAATTAT

*FIG. 12.*

```
  10         20         30         40         50         60         70
GAATTCTTTAATGGTAAAGAACCAAATAGAGGTATAAATCCTTATGAAGCTGTTGCTTATGGTGCTA
 140        150        160        170        180        190        200
CATTAAACTTTAGGTATAGAAAACTGTGGGTGGTATTATGACACAATTAATTAAAAGAAATACTGTCATCC
 270        280        290        300        310        320        330
TTTGAAGGAGAAAGAGCATTAACCAAAGATAATCACCTTTTAGGAAAGTTTGAATTATCTGGTATTCCA
 400        410        420        430        440        450        460
TTACATGTTGAAGCTGAAGACAAAGGTACAGGTAAAAGGTAGAGGTATACTATTACTAATGACAAAGGTAG
 530        540        550        560        570        580        590
AACTTAAGAGAAAAGTTGAAGGCCAAAATAACCTGATAATTATATACAGAGTATGAAAGCAACTGTTGAA
 660        670        680        690        700        710        720
TGTTAAAGATGTTGAAGATTGGTTAAATAATAACTCGAATGTTGATTCTGAAGCATTAAAACAAAATTA
 790        800        810        820        830        840        850
CTTCACCACAACCTAGTGGGAGACGAAGATGTAGATAGTGACGAATTATAAAATCTTCACATTTTATGAAT
 920        930        940        950        960        970        980
TTTAAACAAATTAAAAAAATAACATATATATATGTATATATATATATATATATATATATATATGTATAT
```

FIG. 13A.

```
                     80              90             100            110            120           130
TCCAAGCAGGTATTATTTTAGGTGAAGAATTACAAGAGTTGTTTTATTAGATGTTACTC
       210            220            230            240            250           260
AACCAAAAATCACAAACCTTTTCAACATATCAAGATAACCACCACTGTCTTAATTCAGT
       340            350            360            370            380           390
CCACCACAAAGAGGAGTACCCAAAATTGAAGTTACCTTTACCGTAGACAAAAATGGTATC
       470            480            490            500            510           520
ATTATCGAAAGAACAATCGAAAAAAATGATGAATGCAGAAAATTCGCAGTTGAGATAA
       600            610            620            630            640           650
GATAAAGATAAATTAGCTGATAAATCGAAAAGAAGATAAAAAAATACTATCCTTTCAGC
       730            740            750            760            770           780
AAGATCTTGAAGCTGTATGCCAACCAATCATGTTAAATTATATGGTCAACCAGGAGGAC
       860            870            880            890            900           910
ATATATATTTATTATTATATGTAATATATTTATGCATATTATTATGAATTACCTTCTTTT
       990           1000           1010           1020           1030          1040
AGTTAAATGTATATATAAAAAAAAAACGGAATTC
```

FIG. 13B.

```
          10         20         30         40         50         60
AATCCGTAC TAATGTTGTA ACACCACTTA TCATACAAGC ACAATCAGTA ATGCACTCTA
         130        140        150        160        170        180
TAGATTTGGA TTTGGTTGAA GGATTGTTGT GTCGTAAAAA TGAATTGCCA TATTTGAAAA
         250        260        270        280        290        300
AATCCAATGG TTCAAGAAAA AGTAGTAATA AACAAAAATA TAATGAATCT GATAAAAGAG
         370        380        390        400        410        420
TAAAAGAAAA AGCTAAAACA CTTGGGTAA GTATTATCGT ATTTGATAAT ATGACAGAGA
         490        500        510        520        530        540
ATACATCTGG AACATCTGGG AAACCCAAAG GTGTTATGTT AAGCAATAGG AATTTGTATA
         610        620        630        640        650        660
TATCTTATTT ACCCGTATCT CATATATATG AAAGGGTAT TTTTTTCATT GCTTTGTTT
         730        740        750        760        770        780
ATTCAAAAGC TGAAATTATA TTAGGAGTAC CCAAAGTTTT TAATAGAAATG TATGCAACTA
         850        860        870        880        890        900
ATTACGTAA AGGTAAAAAT AATGGAAATT TCAGTAAAGT TGTTGAAGGT ATTACTAATA
         970        980        990       1000       1010       1020
GGAAATTATC TCCAGAGGT GCTGAGGGTT TAAGTGTTCT ATTAAATGT AAGTATTATC
```

```
            70         80         90        100        110        120
  AATTTAGTAT AGATATAATT ATTGATATAT TAAATAATAC AAAATTAGAA TGGTTGTGTT
           190        200        210        220        230        240
  AGCTGATAAT TTTAGATAAT CTAACTAAGC GTAGTGAAAT GAAGATAGAA AATGAAGAAA
           310        320        330        340        350        360
  AAGACATTAG TTTGTGTGCC TTAGAATGTG ATAAGGAAAA AATAGAAAAG ATTAATTCAT
           430        440        450        460        470        480
  ATAAAATAGC CAATGTTACT GTTCAAAAAG AAGATCCTAA TTTTATTGCC TCTATATGTGT
           550        560        570        580        590        600
  ATGGTGTAAT ACCTCCATGT GATTGTAATA TAATAAAGAA ATATCCTCTA ACAACACATT
           670        680        690        700        710        720
  TGGGTGTAAA GATAAATATA TGGAGTAGAG ATATAAAATT TTTGAATACA GACATATGTA
           790        800        810        820        830        840
  TTATGACGAA AATAAATAAT TTATCACGTT GTAAGAAGTG GATAGCAAAA CAGGCTATAA
           910        920        930        940        950        960
  TATCAAGAAA AATAAAAGAT AAGATAAAACC CTAATATGGA TGTTATCTTA AATGGAGGTG
          1030       1040       1050       1060       1070       1080
  AAGGATATGG TTTAACGAAA TCTACGGGTC CCATATTTTT ACAAGATGTA GATGACTGTA
```

| | | | | | |
|---|---|---|---|---|---|
| 1090 ACACTGAAAG | 1100 TATGGGAGTA | 1110 GCTGTTTCTC | 1120 CTAGTACAAG | 1130 ATACAAAGTA | 1140 AGAACATGGG |
| 1210 TGTTTAGTGG | 1220 ATACTTTTTA | 1230 GAAAAGGAAT | 1240 CTACAGAAACA | 1250 TGCTTTCAAG | 1260 AATGATGGTT |
| 1330 GATCAAAGGG | 1340 TTTGGTTAAA | 1350 TTATCTCAAG | 1360 GTGAATATAT | 1370 AGAAACTGAA | 1380 ATGATAAATA |
| 1450 ATGGACCATT | 1460 GGGAATTATA | 1470 TCTGTGGACA | 1480 AACATAAATT | 1490 ATTTACATTT | 1500 TTAAAAAATG |
| 1570 AAACATTAAA | 1580 TGATCCTATT | 1590 TATGTTGATT | 1600 ATGTAAAGGG | 1610 AAAAATGATG | 1620 GAAATTTATA |
| 1690 GGGACACTAC | 1700 AAACTACCTT | 1710 ACTCCAACAT | 1720 TAAAAATAAG | 1730 AAGATTCAAT | 1740 GTATTTAAAG |
| 1810 GCACGGGTAG | 1820 TATGAATAAT | 1830 GGTAAAAGTG | 1840 GAAGTAAATC | 1850 TGATATTAAA | 1860 GGTGGAAGTA |
| 1930 AAGTGGAAG | 1940 TAAAGATGAT | 1950 ATAAAAGTG | 1960 GAAGTAAAGA | 1970 GAAGTAAAGA | 1980 TCATATAAAA CGGAATT |

FIG. 14C.

| 1150 | 1160 | 1170 | 1180 | 1190 | 1200 |
|---|---|---|---|---|---|
| AAATTTATAA | GGCTACAGAT | ACTATACCAA | AAGGAGAAT | GTTAATTAAA | AGTGATTCTA |
| 1270 | 1280 | 1290 | 1300 | 1310 | 1320 |
| ATTTTAAAAC | GGGAGATATT | GTACAAATTA | ATGATAATGG | TTCTTTAACA | TTTTTAGATA |
| 1390 | 1400 | 1410 | 1420 | 1430 | 1440 |
| ATTTATATTC | CCAAATCCCT | TTTGTAAATT | TTTGTGTTGC | ATATGGTGAT | GATTCTATGG |
| 1510 | 1520 | 1530 | 1540 | 1550 | 1560 |
| ATAATATGTT | AAAGACAACT | GGTGTAGATG | AGAAAAATT | TTCAGAAAAA | TTAATTGATG |
| 1630 | 1640 | 1650 | 1660 | 1670 | 1680 |
| AAAAAACTAA | TTTAAATAGA | TACAATGTTA | TTAATGACAT | ATACTTAACT | TCCAAACCAT |
| 1750 | 1760 | 1770 | 1780 | 1790 | 1800 |
| ATTTTTCTTT | TTTTATAGAT | GAAGTTAAAA | AGAAATATGA | AGAAAAATTA | AGTGGAAGTA |
| 1870 | 1880 | 1890 | 1900 | 1910 | 1920 |
| AAGATGATAT | AAAAAGTGGA | AGTAAAGATG | ATATAAAAAG | TGGAAGTAAA | GCTGATATAA |
| 1990 | 2000 | 2010 | 2020 | 2030 | 2040 |

FIG. 14D.

ASEXUAL BLOOD STAGE ANTIGENS OF *PLASMODIUM FALCIPARUM* WHICH ENCODE A RHOPTRY PROTEIN

This invention relates to synthetic peptides and polypeptides which have antigenicity suitable for providing protective immunity against *Plasmodium falciparum* infections, and to methods for the production thereof.

The human malaria parasite *Plasmodium falciparum* encodes many polypeptides that elicit an immune response in man. Recently, molecular cloning techniques have facilitated the analysis of individual polypeptide antigens that are present in this complex mixture (1). Many cDNA clones encoding these antigens have been isolated by screening *Escherichia coli* colonies that express the cloned sequences with human antibodies. The production and screening of these clones is described in detail in International Patent Specification No. PCT/AU84/00016.

The present invention is based upon the identification and characterisation of further asexual blood-stage antigens of *P. falciparum*.

According to the present invention, there is provided a DNA molecule comprising a nucleotide sequence substantially corresponding to all or a portion of a base sequence coding for one of the antigens of *P. falciparum* described in detail hereinafter. In particular, there is provided a DNA molecule comprising a nucleotide sequence characterized by at least a portion thereof comprising all or a portion of a base sequence shown in the accompanying Figures. Such a nucleotide sequence codes for a polypeptide comprising at least a portion which corresponds to a portion of the amino acid sequence of an antigen of *P. falciparum* as described herein.

The present invention also extends to synthetic peptides or polypeptides displaying the antigenicity of all or a portion of an antigen of *P. falciparum* as described herein, as well as to compositions for stimulating immune responses against such an antigen in a mammal, which compositions comprise at least one synthetic polypeptide displaying the antigenicity of all or a portion of the antigen, together with a pharmaceutically acceptable carrier therefor. The synthetic peptides or polypeptides according to this aspect of the invention may be prepared by expression in a host cell containing a recombinant DNA molecule which comprises a nucleotide sequence as broadly described above operatively linked to an expression control sequence, or a recombinant DNA cloning vehicle or vector containing such a recombinant DNA molecule. The synthetic peptide or polypeptide so expressed may be a fusion peptide comprising in addition to a portion displaying the antigenicity of all or a portion of the antigen, an additional polypeptide coded for by the DNA of the recombinant DNA molecule. Alternatively, the synthetic peptides or polypeptides may be produced by chemical means, such as by the well-known Merrifield solid-phase synthesis procedure.

(I) A RHOPTRY PROTEIN OF *P. falciparum*

Intraerythrocytic asexual parasites of *Plasmodium falciparum* are responsible for the morbidity and mortality of this serious protozoal infection of man. Propagation of the asexual parasite occurs when mature schizonts rupture and release merozoites which invade fresh erythrocytes. Invasion begins when the merozoite abuts an erythrocyte and re-orientates so that the apex of the merozoite is in contact with the erythrocyte membrane. Paired apical organelles called rhoptries discharge their contents prior to perturbation of the erythrocyte membrane and subsequent entry of the merozoite. Rhoptry proteins have been implicated as potential protective immunogens in several systems (2, 3). A cDNA clone encoding a portion of a Mr 105,000 rhoptry protein of *P. falciparum* has now been identified and characterised. A rhoptry protein of this molecular weight is present in several isolates of *P. falciparum* from widely separated geographical areas.

Several previously isolated cDNA clones expressing *P. falciparum* antigens contained regions of tandemly repeated peptides. It has previously been shown that these repeat regions are frequently highly antigenic and are the immunodominant regions of the molecule recognized during natural infection. The clone Ag44 expressing part of the Mr 107,000 rhoptry protein is an example where a naturally antigenic determinant is encoded by non-repeat sequence. It is not known whether other portions of this molecule contain repeat regions. The identification of this clone allows the preparation of monospecific reagents against this rhoptry protein which will enable tests of its function and potential as a protective immunogen.

Further details of the isolation and characterization of this protein will be apparent from the following detailed description, and from the accompanying figures. In the figures:

FIG. 1 shows indirect immunofluorescence of the FC27 isolate of *P. falciparum* asexual blood stages reacted with human antibodies against Ag44. Fluorescein staining of FIG. 1A, a late trophozoite (T) and early schizont (S) exhibiting weak fluorescence excluded over the nuclei; FIG. 1B, a mature schizont with the predominant pattern of punctate fluorescence (left) and a multiply-infected erythrocyte exhibiting both punctate and lattice patterns of fluorescence (right); FIG. 1C, punctate fluorescence associated with extracellular merozoites. Paired spots of fluorescent staining occur within a single merozoite (arrowed). Inset is of a mature schizont from an adjacent field of view.

FIG. 2 shows immunoelectron microscopy, using the protein A-gold technique, of a schizont of the FC27 isolate of *P. falciparum* reacted with human antibodies against Ag44. The pear-shaped rhoptries containing antigen reacting with antibodies are arrowed. (Magnified $\times 79,000$.)

FIG. 3 shows immunoblots using human antibodies affinity-purified on the fusion protein of clone Ag44. FIG. 3A—Identification of the corresponding parasite antigen in different life-cycle stages of FC27: uninfected cells (1), rings (2), trophozoites (3), schizonts (4), merozoites (5). FIG. 3B—Identification of the corresponding parasite antigen in 4 different isolates of *P. falciparum* grown in asynchronous culture: NF7 (1), K1 (2), FC27 (3) and V1 (4).

FIG. 4 is the nucleotide and amino acid sequence of Ag44. At the 5' end of the insert the first 2 bases derived from *P. falciparum* put the sequence in frame with β-galactosidase but are not translated here because the corresponding hybrid codon would not be found in the *P. falciparum* sequence.

Materials and Methods (See later)

RESULTS

Identification of a cDNA Encoding a Rhoptry Protein cDNA derived from the Papua New Guinea isolate FCQ27/PNG (FC27) isolate of *P. falciparum* was prepared as described and inserted into the expression vector λgt11-Amp3 (1). A large number of clones expressing *P. falciparum* sequences were screened with human antibodies affinity purified against the FC27 isolate and seventy-eight antigen positive clones were identified (4). One such clone, Ag44, was shown to encode part of a rhoptry protein as follows. *E. coli* lysogenic for λAg44 were grown in liquid culture, heat-induced, lysed and coupled to CNBr-activated Sepharose. Human antibodies specific for the Ag44 fused polypeptide were affinity purified on this absorbent, and used to identify the *P. falciparum* protein corresponding to Ag44 by immunofluorescence and immunoblot assays.

Asynchronous cultures of the FC27 isolate were fixed to glass slides and examined by direct immunofluorescence. Proteins reactive with anti-Ag44 antibodies were localised to mature schizonts, in paired organelles within merozoites, a pattern characteristic of rhoptry proteins (FIG. 1a). Little reactivity was seen with ring forms. Several different isolate of *P. falciparum*: K1 from Thailand, NF7 from Ghana and V1 from Vietnam, all showed identical patterns of fluorescence.

Immunoelectron microscopy confirmed the rhoptry location of the antigen recognised by anti-Ag44 antibodies. There was heavy labelling of the pear-shaped organelles when sections of schizonts were incubated first with affinity purified human anti-Ag44 antibodies and then protein A-gold (FIG. 2).

Figures 3A, 3B:
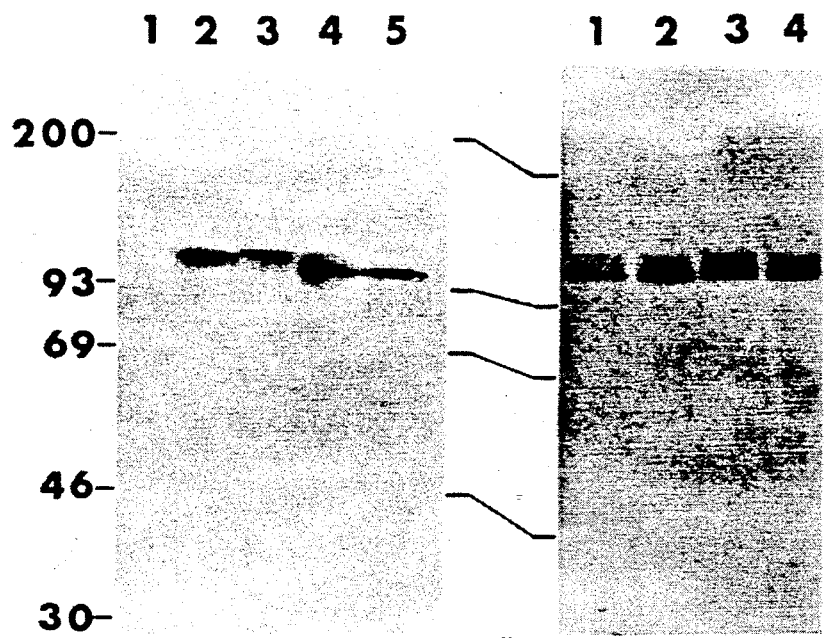

Immunoblot analysis of lysates of synchronized *P. falciparum* infected cells showed that the anti-Ag44 antibodies recognised 3 closely-spaced bands of Mr 107,000, 105,000 and 103,000 (FIG. 3a). The higher molecular weight forms were more prominent in immature forms, and this may suggest a precursor product relationship. A similar set of bands was recognised when lysates of several different *P. falciparum* isolates were probed with anti-Ag44 antibodies (FIG. 3b).

Nucleotide Sequence of Ag44

DNA was purified from phage expressing Ag44. Only 1 insert was present and this was subcloned into the pUC and M13 vectors. The nucleotide sequence of the 494 bp R1 fragment was determined by the dideoxy method (FIG. 4). There was a long open reading frame present which extended up to nucleotide 404 and was in frame with β-galactosidase, accounting for the large fused polypeptide synthesized by λAg44 (4). The predicted amino acid sequence is displayed (FIG. 4). There are *no* tandemly repeated peptide elements as are commonly found in other *P. falciparum* antigens. The termination codon at nucleotides 405–407 presumably represents the 3' end of the coding region. This is consistent with the presence of deoxyadenosine bases present at the extreme 3' end of the DNA sequence which correspond to the poly(A) tail of the mRNA. This sequence predicted here would encode approximately 16% of the entire molecule.

Genomic Context of Ag44

Figures 5A, 5B:
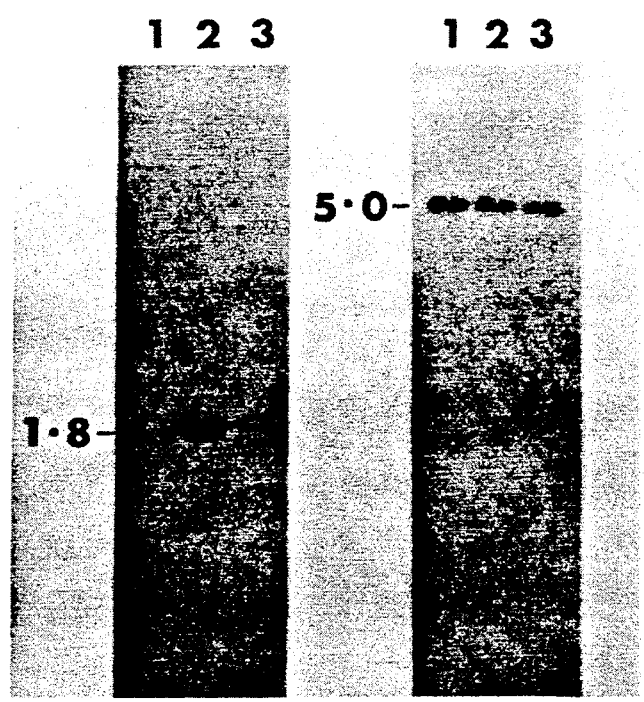
FIG. 5 shows the hybridization of Ag44 cDNA to restriction fragments of *P. falciparum* DNA. DNA from isolates FC27 (1), K1 (2) and NF7 (3) was cleaved with EcoRI FIG. 5A and Hind 3 FIG. 5B, fractionated by electrophoresis on a 1% agarose gel, blotted to nitrocellulose, hybridized with $^{32}$P-Ag44 cDNA and autoradiographed.

DNA from three *P. falciparum* isolates FC27, K1 and NF7 was cleaved with EcoRI or AhaIII; size fractionated and blotted to nitrocellulose. The purified 570 bp R1 fragment of Ag44 was nick-translated and hybridized to the nitrocellulose filter. All isolates showed a common band of 1800 bp in EcoR1 digests and 5000 bp in Hind 3 digests (FIG. 5).

(II) AN ACIDIC BASIC REPEAT ANTIGEN (ABRA) OF *P. falciparum*

A Mr 102,000 antigen of *P. falciparum*, predominantly of schizonts, has been identified and characterized. Sequencing studies on 4 cDNA clones encoding parts of this antigen revealed blocks of hydrophilic dipeptide and tripeptide repeats and so the antigen has been designated the Acidic Basic Repeat Antigen (ABRA).

Further details of the isolation and characterisation of this antigen will be apparent from the detailed description hereunder, and from the accompanying figures. In the figures:

FIG. 6 shows indirect immunofluorescence of *P. falciparum* a sexual blood stages reacted with human antibodies to Ag196. Single fields of view for isolate V1 (FIGS. 6A and B) and FC27 (FIGS. 6C and D) examined by fluorescein (A, C) and propidium (B, D) fluorescence the erythrocytes shown contain trophozoites (T) and schizonts (S).

FIG. 7 shows immunoblots using human antibodies affinity-purified on the fusion protein of clone Ag196.

Figure 7A:
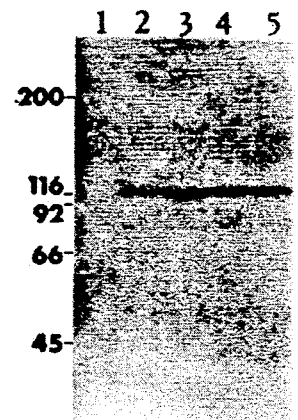

FIG. 7A. Identification of ABRA in 4 different isolates of *P. falciparum* grown in asynchronous culture: uninfected red cells (1), NF7 (2), K1 (3), FC27 (4) and V1 (5).

Figure 7B:
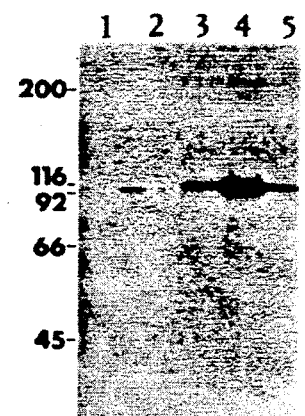

FIG. 7B. Detection of ABRA in different life-cycle stages of FC27: uninfected red cells (1), rings (2), trophozoites (3), schizonts (4) and merozoites (5).

Figure 7C:
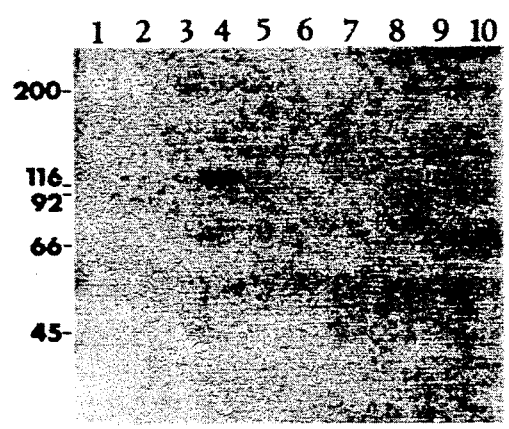

FIG. 7C. Triton X-100—extracts of the same life-cycle stages as in (B) (lane 1 to 5). Triton-insoluble pellets were resolubilized in NaDodSO$_4$: uninfected cells (6), rings (7), trophozoites (8), schizonts (9) and merozoites (10). Molecular weight markers are myosin (200 kD), β-galactosidase (116 kD), phosphorylase D (92 kD), bovine serum albumin (66 kD) and ovalbumin (45 kD).

FIG. 8A–C is the nucleotide and amino acid sequence of Ag189. The start of Ag144, Ag196 and Ag 126 in relation to Ag189 are indicated by arrows and the adjacent clone number.

Figure 9:
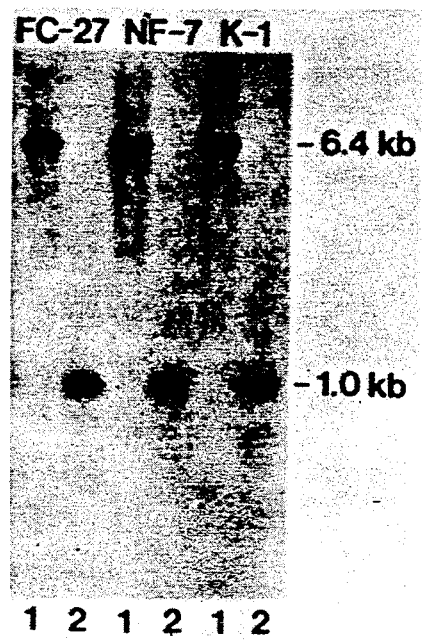

FIG. 9 shows hydridization of Ag126 cDNA to restriction fragments of *P. falciparum* DNA. DNA from the 3 isolates of *P. falciparum* indicated was cleaved with EcoRI (1) and Aha III (2), fractionated by electrophoresis on a 1% agarose gel, blotted to nitrocellulose, hybridized with $^{32}$P-Ag126 cDNA and autoradiographed. The *P. falciparum* isolates were: FC27 from Papua New Guinea; NF7 from Ghana and K1 from Thailand.

Materials and Methods (See later)

RESULTS

ABRA is located in the mature schizont

Figure 6A:
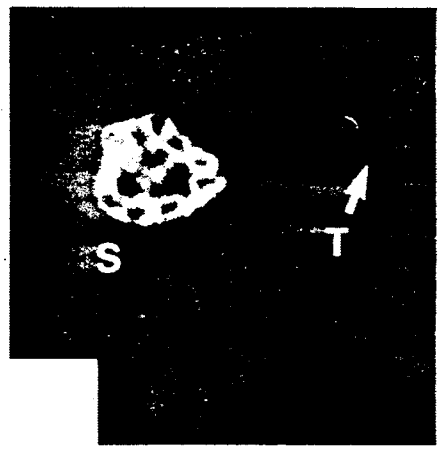
Figure 6C:
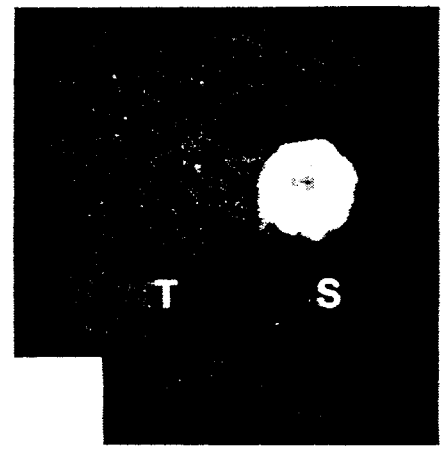
Figure 6B:
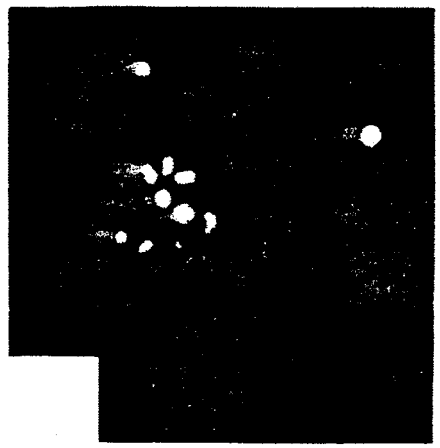
Figure 6D:

Indirect immunofluorescence was performed on acetone-fixed, asexual blood-stage parasites using human antibodies affinity-purified on an immunoadsorbent of Ag196. The antibodies reacted strongly with erythrocytes containing schizonts and gave predominantly a lattice pattern of fluorescence which is particularly well resolved in isolate V1 (FIG. 6A). Counterstained nuclei of the developing merozoites appeared within regions that excluded fluorescein staining (FIG. 6B). Little or no reactivity was seen with ring and trophozoite stages of V1.

More intense fluorescence was observed at a given antibody dilution with isolate FC27. Staining again occurred predominantly with erythrocytes containing schizonts, but there was diffuse staining in trophozoites to a greater extent than with V1 (FIG. 6C). Fluorescence of the surface of infected erythrocytes was not seen when the assay was performed using unfixed cells or lightly glutaraldehyde-fixed and air-dried monolayers (5). Similar results with FC27 were obtained using mouse antisera against clones Ag196, Ag189, Ag126 and Ag203 belonging to the same serological family.

In immunoblots of asynchronous parasite preparations, affinity-purified human antibodies against clone Ag196 detected a dominant band of Mr 102,000, which did not vary between the 3 isolates NF7, FC27 and V1 (FIG. 7A). The corresponding protein is approximately Mr 2,000 smaller in isolate K1 from Thailand (FIG. 7A).

In immunoblots of life-cycle stages (FIG. 7B) the dominant Mr 102,000 band was present in schizonts was poorly represented or absent from other stages. A weak band of Mr 230,000 was also present in schizont preparations (FIG. 7B). The target antigen was recovered in Triton extracts of infected erythrocytes and no additional material was detected by anti-Ag196 antibodies when pellets were resolubilized in NaDodSO$_4$ sample buffer (FIG. 7C).

Nucleotide and amino acid sequence

The cDNA inserts of 4 members of the Ag196-family were isolated. The insert of Ag189 was subcloned into the vector M13mp8 and its nucleotide sequence determined by the dideoxy procedure. Ag189 contains an insert of 965 bp, which has a single open reading frame extending through the whole cDNA. This frame is shown in FIG. 8. All the other frames are interrupted by multiple stop codons. Ag189 is not in frame with β-galactosidase and does not produce a large fused polypeptide. A number of other clones from similar expression libraries were out of phase with β-galactosidase (6).

Hydrophilic dipeptide and tripeptide repeats predicted from the sequence of ABRA The sequence of Ag189 from position 1 to 834 encodes predominantly hydrophilic amino acids. At the 3' end starting at position 835 extends a highly charged region which consists of 10 dipeptide repeats (Glu-Lys) and 6 interspersed tripeptide repeats (Glu-Glu-Lys). The repeat-block is flanked on either side by three glutamic acids.

Three blocks of 12 nucleotides starting from position 678 to 714 exhibits a high degree of homology. These "cryptic" dodeca-nucleotide repeats only show a minor degree of similarity on the amino acid level. Asparagine and isoleucine in position 3 and 4 in the first repeat appear again in the same position in the third repeat and glutamines were found in position 1 and 2 of the second and the third cryptic repeat.

A dodecapeptide was synthesized comprising the amino acid sequence Glu-Lys-Glu-Glu-Lys-Glu-Lys-Glu-Glu-Lys-Glu-Lys and the binding of antibodies in malarial sera from PNG to this peptide was tested by a radioimmunoassay (RIA). The malarial sera gave no signal in the RIA. This result was surprising because synthetic peptides corresponding to six other repeating sequences that have been determined in other antigens of P. falciparum all gave positive results (7, 8, 15).

In order to exclude sequencing errors the complete nucleotide sequence of Ag189 was again determined and an identical sequence and reading frame was obtained. In addition, the inserts of 3 further clones were sequenced, namely Ag126, Ag144 and Ag196 coding for segments of the same P. falciparum. These 3 clones are all in phase with β-gal, produce large fused polypeptides and exhibit the same open reading frame as Ag189. Therefore there is certainty about the reading frame. The sequence of Ag126, 144 and 196 includes in all 3 clones the region with the block of di- and tripeptide repeats. However differences among the 4 cDNA clones were also noted.

Ag144 which is 581 bp long commences at position 387 in relation to Ag189 and has deleted 6 bp in position 950 to 955, but contains 7 additional As at the 3' end of the cDNA, which codes for two more lysines. Ag126 and Ag196 are 451 and 452 bp long respectively and both start at position 458 in relation to Ag189. The Ag126- and Ag196-insert exhibit a deletion extending from position 901 to 955 in the sequence shown in FIG. 8. It is believed that these deletions are artefacts of clonging in M13. Similar problems of maintaining cDNA inserts in M13 have been observed with other malarial antigens (15).

Ag126 and Ag196 both differ from the sequence of Ag189 and Ag144 in two nucleotides. Ag126 and Ag196 contain at position 461 (in relation to Ag189) a "T" instead of an "A", replacing tyrosine by phenylalanine and in position 806 a "T" instead of "C", which has no effect at the amino acid level. Ag126 and Ag196 have 3 and 4 additional As at the 3' end coding for 1 and 2 more lysines, respectively.

Genomic organisation of ABRA

The insert of Ag126 was used in Southern blot experiments to investigate the genomic organisation of ABRA. DNA from 3 geographical isolates of P. falciparum, the homologous strain FC27 from Papua New Guinea, NF7 from Ghana and K1 from Thailand were restricted with EcoRI and AhaIII, size-fractionated on 1% agarose gels, blotted on nitrocellulose and probed with the $^{32}$p-labelled insert of Ag126. As can be seen in FIG. 9, the insert hybridized to a single 6.4 kb EcoRI fragment and a 1 kb AhaIII fragment in each isolate investigated. In addition, the DNAs of a further 3 isolates from Papua New Guinea (IMR143, IMR144 and MAD71) were probed with the 581 bp insert of Ag144 and showed identical fragment sizes in these isolates (data not shown).

III OTHER ANTIGENS CLONED IN E. coli

Several other antigens of P. falciparum, which are natural immunogens in man (and therefore potential vaccine candidates), have been identified with antibodies raised against or affinity purified on P. falciparum antigens expressed from cDNA sequences cloned in E. coli using the λAmp3 vector. The clones, and the apparent molecular weights and stage specifities (determined by immunofluorescent microscopy) of the corresponding parasite antigens, are listed in Table 1.

FIG. 10A-B is the nucleotide sequence of clone Ag169;

FIG. 11 is the nucleotide sequence of clone Ag303;

FIG. 12 is the nucleotide sequence of clone Ag358;

FIG. 13A-B is the nucleotide sequence of clone Ag361;

FIGS. 14A-D show the nucleotide sequence of clone Ag394; and

FIG. 15 shows indirect immunofluorescence on acetone-methanol fixed bloodstages of P. falciparum reacted with antibodies directed against antigens produced by Ag501 in bacteria T.—trophozoite (minimal reaction). S-schizont. G.—gametocyte (no reaction seen).

TABLE 1

| Clone | Corresponding P. falciparum Antigen | |
|---|---|---|
| | Apparent Molecular Weight (Mr)* | Predominant Location by Immunofluorescence |
| Ag169 | N.A. | N.A. |
| Ag303(Ag331)** | 125,000-130,000 | Schizonts |
| Ag358 | Dominant bands are 210,000; 190,000 and 140,000 | All stages |
| Ag361 | 70,000 | Mature stages |
| Ag372 | 195,000; 140,000 and 80,000 | Mature stages |
| Ag394 | 140,000*** | All stages including rhoptry locations. |
| Ag501 | ~130,000 | Mature stages |

N.A. - Not available
*The apparent molecular weights (Mr) have been determined by Western blotting from 7.5% gels using antigens from the FC27 P. falciparum isolate. In some cases, the Mr can vary considerably in other isolates and of other gel conditions are employed. Also in some cases numerous other weaker bands are seen, presumably reflecting breakdown products or cross-reactions.
**It has been found that Ag303 and Ag331 correspond to fragments of the one coding sequence.
***Cross-reactions with Ag23 and with bands of 105,000 and 102,000 were also observed.

MATERIALS AND METHODS

Parasites

P. falciparum isolates FCQ27/PNG (FC27), IMR143, IMR144 and MAD71 were obtained through the Papua New Guinea Institute of Medical Research. NF7 from Ghana, and K1 from Thailand, were obtained from D. Walliker, Edinburgh University. V1 from Vietnam was obtained from L. Miller, National Institute of Health, Bethesda, U.S.A. Parasites were maintained in asynchronous in vitro culture in Group O human erythrocytes according to Trager and Jensen (9). To obtain stage-specific life-cycle forms, parasite cultures were synchronised twice to within a six hour spread of maturation using sorbitol (10) and harvested at various time points of the asexual cycle. Naturally released merozoites were obtained as described previously (11).

Sera

Sera were obtained with informed consent from individuals living in the Madang region of Papua New Guinea. Some patients presented with acute malaria while in others, asymptomatic parasitaemia was detected in the course of routine surveys. Parasitaemic individuals were treated with chloroquine and convalescent serum was collected one or two weeks later. Parental consent was obtained before taking samples from children. In all cases, serum was separated and stored at $-20°$ C. for up to 12 months then held at $-70°$ C. Presence or absence of splenomegaly was documented for some subsets and parasiteaemia was assessed from a thick blood smear in all cases.

Clones Expressing P. falciparum Antigens

Methods for construction of the P. falciparum cDNA expression library and isolation of clones by antibody screening have been published (1). Replicas of the antigen-positive clones were grown overnight at 30°, induced at 38°, and lysed in situ as described (12). Individual human sera were pretreated to remove anti-E. coli activity, reacted with the colonies at a final dilution of 1:500 in 3% bovine serum albumin/Tris saline, pH 9.6 albumin, and the colonies then reacted with $^{125}$I protein A from Staphylococcus aureus and autoradiographed as described (12).

HYBRIDIZATION EXPERIMENTS

DNA carrying inserts were purified by CsCl centrifugation, digested with EcoRI, end-labelled with $^{32}$P-dATP by the Klenow fragment of DNA polymerase I and size-fractionated on a 1% low-melting agarose-gel. The labelled inserts were recovered and hybridized to the bank of antigen-positive clones. In some cases the insert was first subcloned in the plasmid pUC-9 (13) purified by gel electrophoresis and then nick translated. Inserts which had been subcloned in this way were used in Southern blot experiments. For Southern blots, two micrograms of parasite DNA was digested with restriction, endonuclease according to the manufacturer's instructions, electrophoresed in a 1% agarose gel and blotted to nitrocellulose filters which were then hybridised with $10^6$ cpm/ml of the various probes.

NUCLEOTIDE SEQUENCE DETERMINATION

The dideoxy chain termination method (14), was employed for sequence determination. The inserts of the various antigen-expressing clones and fragments generated by digestion with appropriate restriction endonucleases were cloned onto M13mp8 and/or M13mp9 (13).

AFFINITY PURIFICATION OF HUMAN ANTIBODIES AGAINST CLONED MALARIA ANTIGENS

Induced 50 ml cultures of antigen positive clones were prepared as described previously (15). The pelleted bacteria were sonicated and soluble proteins were conjugated to CNBr-activated Sepharose (Pharmacia, Sweden). Antibodies from a pool of human plasma were affinity-purified on the immobilised antigen as described (15).

INDIRECT IMMUNOFLUORESCENCE

Thin blood films of parasitized erythrocytes from asynchronous cultures of P. falciparum were fixed in 90% acetone/10% methanol and reacted with affinity-purified human antibodies. Sera from mice immunized with bacterial lysates of antigen-positive clones were also examined (16). Fluorescein-conjugated sheep anti-human Ig or sheep anti-mouse Ig antisera were used as the second antibody. Parasite nuclei were counterstained with propidium iodide and the slides were mounted in 90% glycerol/10% PBS containing p-phenylenediamine for viewing under U.V. illumination.

IMMUNOELECTRON MICROSCOPY

Parasitized erythrocytes were fixed with glutaraldehyde, sectioned after being embedded in L. R. White resin and incubated with appropriately diluted antibodies and protein A-gold using published procedures (11).

IMMUNOBLOTTING

Merozoites and infected erythrocytes containing either stage-specific or asynchronous parasites were diluted in sample buffer containing 3% SDS, 62.5 mM Tris-HCl, β-mercaptoethanol, pH 6.8 and heated for 2 min at 100° C. After centrifugation at 12,000 g for 10 min., protein extracts were fractionated on 7.5% or 10% polyacrylamide/SDS gels and transferred electrophoretically to nitrocellulose. Filters were blocked with 5% non-fat milk powder in phosphate-buffered saline (PBS) pH 7.4 and reacted with affinity purified human antibodies. They were then incubated in $^{125}$I-labelled protein A and autoradiographed.

In a separate experiment, parasitized cells and merozoites were first incubated in PBS containing 0.5% Triton X-100, 5 mM PMSF, 1 mM TPCK, 2.5 mM EDTA and 2 mM iodo-acetamine for 30 mins at room temperature and centrifuged at 12,000 g for 10 min. Supernatants and pellets were then individually diluted to equivalent final volumes in sample buffer and treated as before.

REFERENCES

1. Kemp, D. J., Coppel, R. L., Cowman, A. F., Saint, R. B., Brown, G. V. and Anders, R. F. (1983) *Proc. Natl. Acad. Sci. USA* 80, 3787-3791.
2. Holder, A. A. and Freeman, R. R. (1981) *Science*, 193, 673-676.
3. Perrin, L., Chizzolini, C., Lebon, H., Shaw, A., Merkli, B. and Stocker, J. In "Proc. Asia & Pacific Conference on Malaria", Honolulu, Hawaii, USA, Apr. 21-27, 1985.
4. Anders, R. F., Coppel, R. L., Brown, G. V., Saint, R. B., Cowman, A. F., Lingelbach, K. R., Mitchell, G. F. and Kemp, D. J. (1984) *Molec. Biol. Med.* 2, 177-191.
5. Perlmann, H., Berzins, K., Wahlgren, M., Carlsson, J., Björkmann, A., Patarvoyo, M. E. and Perlman, P. (1984) *J. Exp. Med.* 159, 1686-1704.
6. Dame, J. B., Williams, J. L., McCutchan, T. F., Weber, J. L., Wirtz, R. A., Hockmeyer, W. T., Sanders, G. S., Reddy, E. P., Maloy, W. L., Haynes, J. D., Schneider, I., Roberts, D., Diggs, C. L. and Miller, L. H. (1984) *Science* 225, 593-599.
7. Coppel, R. L., Cowman, A. F., Lingelbach, K. R., Brown, G. V., Saint, R. B., Kemp, D. J. and Anders, R. F. (1983) *Nature* (London) 306, 751-756.
8. Coppel, R. L., Cowman, A. F., Anders, R. F., Bianco, A. E., Saint, R. B., Lingelbach, K. R., Kemp, D. J. and Brown, G. V. (1984) *Nature* (London) (in press).
9. Trager, W. and Jensen, J. B. (1976) *Science* 193, 673-676.
10. Lambros, C. and Vanderberg, J. P. (1979) *J. Parasitol* 65, 418.
11. Brown, G. V., Culvenor, J. G., Crewther, P. E., Bianco, A. E., Coppel, R. L., Saint, R. B., Stahl, H-D, Kemp, D. J. and Anders, R. F. (1985) *J. Exp. Med* 162, 774-779.
12. Stahl, H-D., Coppel, R. L., Brown, G. V., Saint, R. B., Lingelbach, K., Cowman, A. F., Anders, R. F. and Kemp, D. J. (1984) *Proc. Nat. Acad. Sci. USA* 81, 2456-2460.
13. Messing, J. and Vieira, J. (1982) *Gene* 19, 269-276.
14. Sanger, R., Nicklen, S. and Coulson, A. R. (1977) *Proc. Nat. Acad. Sci. USA* 74, 5463-5467.
15. Stahl, H-D., Crewther, P. E., Anders, R. F., Brown, G. V., Coppel, R. L., Bianco, A. E., Mitchell, F. G. and Kemp, D. J. (1985) *Proc. Nat. Acad. Sci. USA* 82, 543-547.
16. Coppel, R. L., Brown, G. V., Mitchell, G. F., Anders, R. F. and Kemp, D. J. (1984) *EMBO J.* 3, 403-407.

We claim:

1. An isolated and purified DNA molecule comprising: a nucleotide sequence encoding an antigen of *P. falciparum* selected from the group consisting of:
   a $M_r$ 103,000 Rhoptry Protein,
   a $M_r$ 105,000 Rhoptry Protein, and
   a $M_r$ 107,000 Rhoptry Protein.

2. A DNA molecule according to claim 1 which is the nucleotide sequence shown in FIG. 4 or a portion thereof encoding an antigenic peptide.

3. A DNA molecule comprising: a recombinant DNA molecule containing a nucleotide sequence capable of expressing an antigen of *P. falciparum* selected from the group consisting of:
   a $M_r$ 103,000 Rhoptry Protein,
   a $M_r$ 105,000 Rhoptry Protein, and
   a $M_r$ 107,000 Rhoptry Protein.

4. A DNA molecule according to any one of claims 1 to 3, operatively linked to an expression control sequence.

5. A DNA vector comprising: a nucleotide sequence of any one of claims 1 to 3 or a portion thereof encoding an antigenic peptide, wherein said sequence is operatively linked to an expression control sequence.

6. A DNA vector comprising: a nucleotide sequence of any one of claims 1 to 3 or a portion thereof encoding an antigenic peptide, wherein said sequence is operatively linked to an expression control sequence and inserted into a bacteriophage.

7. A host cell containing a DNA molecule according to claim 4.

8. A host cell containing a DNA vector according to claim 5.

* * * * *